(12) United States Patent
Shioyama et al.

(10) Patent No.: US 9,970,872 B2
(45) Date of Patent: May 15, 2018

(54) CELL ANALYZER AND CELL ANALYZATION METHOD

(75) Inventors: Takahiro Shioyama, Tokyo (JP); Akane Suzuki, Tokyo (JP); Sunao Takeda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1787 days.

(21) Appl. No.: 13/217,338

(22) Filed: Aug. 25, 2011

(65) Prior Publication Data

US 2012/0052491 A1     Mar. 1, 2012

(30) Foreign Application Priority Data

Aug. 26, 2010   (JP) ................................ 2010-189920

(51) Int. Cl.
| | | |
|---|---|---|
| G01N 33/48 | (2006.01) | |
| G01N 21/64 | (2006.01) | |
| G01N 15/14 | (2006.01) | |
| G01N 15/10 | (2006.01) | |

(52) U.S. Cl.
  CPC ..... *G01N 21/6428* (2013.01); *G01N 15/1459* (2013.01); *G01N 2015/1006* (2013.01); *G01N 2015/1402* (2013.01); *G01N 2015/1488* (2013.01)

(58) Field of Classification Search
  CPC ................................................. G01N 21/6428
  USPC ......................................................... 702/19
  See application file for complete search history.

(56) References Cited

U.S. PATENT DOCUMENTS

| 4,741,043 A | 4/1988 | Bacus |
|---|---|---|
| 2004/0042646 A1 | 3/2004 | MacAulay et al. |
| 2009/0091746 A1 | 4/2009 | Fukuda et al. |
| 2010/0196917 A1 | 8/2010 | Ishisaka et al. |
| 2014/0154677 A1 | 6/2014 | Ishisaka et al. |

FOREIGN PATENT DOCUMENTS

| JP | 7-146289 A | 6/1995 |
|---|---|---|
| JP | 2004-73198 A | 3/2004 |
| JP | 2005-536752 A | 12/2005 |
| JP | 2009-103687 A | 5/2009 |
| WO | 2009/057525 A1 | 5/2009 |

OTHER PUBLICATIONS

Office Action, dated Sep. 18, 2013, issued by the Japanese Patent Office in counterpart Japanese Patent Application No. 2010-189920.
Office Action, dated May 13, 2013, issued by the Japanese Patent Office in counterpart Japanese Patent Application No. 2010-189920.
Itoi, Hirosumi, et al., "Analysis of DNA Ploidy Pattern," Clinical Gastroenterology, vol. 10, No. 12, 1995, pp. 1741-1748.
Kawamoto, Keiji, et al., "Imaging of Laser Scanning Cytometer," Medical Imaging Technology, vol. 17, No. 3, 1999, pp. 197-202.
Ogawa, Masahisa, et al., "Significance of DNA Ploidy Pattern in Diagnosis of Ovarian Tumor," The Journal of the Japanese Society of Clinical Cytology, vol. 28, No. 1, 1989, pp. 48-55.
Notification of Reasons for Refusal dated Dec. 15, 2015 by the Japanese Patent Office in related Application No. 2015-019165.

*Primary Examiner* — Jerry Lin
(74) *Attorney, Agent, or Firm* — Sughrue Mion, PLLC

(57) ABSTRACT

A cell analyzer includes: a measuring portion which measures cells that are nuclear stained; a displaying portion which displays a histogram of a fluorescence intensity by using a result of the measurement by the measuring portion; and a determining unit which obtains a number of strong-area cells that are distributed in an area where the fluorescence intensity is stronger than normal cells, and which determines a malignancy grade of cancer based on the number of strong-area cells and the histogram.

8 Claims, 12 Drawing Sheets

FIG. 13A

|  | | EMBODIMENT | | | |
|---|---|---|---|---|---|
|  | | 0 | 2 | 3 | 4 |
| PATHOLOGICAL ANALYSIS | 0 | 36 | 10 | 0 | 0 |
|  | 2 | 5 | 43 | 7 | 3 |
|  | 3 | 0 | 5 | 14 | 5 |
|  | 4 | 0 | 3 | 6 | 18 |

FIG. 13B

| | |
|---|---|
| True negative | 78%(36/46) |
| False positive | 22%(10/46) |
| False negative | 5%(5/109) |
| True positive | 95%(104/109) |

CELL ANALYZER AND CELL ANALYZATION METHOD

BACKGROUND OF THE INVENTION

The present invention relates to a cell analyzer and a cell analyzation method.

After a pathological specimen is prepared, a pathological diagnosis on a tissue slice is performed by a cytotechnologist or a pathologist.

A skilled technique is required for preparing a specimen or performing a diagnosis by a cytotechnologist or a pathologist, and there is a possibility that a difference may be produced in the diagnosis result depending on the difference in technique. In the period from extraction of tissue to diagnosis, procedures such as tissue fixation, section preparation, and staining are necessary, and a cytotechnologist or the like is restrained for a predetermined time period. Therefore, procedures which are to be performed before diagnosis are requested to be automatized.

Moreover, also determination whether tissue extracted during an operation is tumor tissue or normal tissue is required depending on the portion of a tumor or the operative method. Therefore, a rapid diagnosis due to cytoscreening or a frozen slice is performed. As compared with a usual pathological analysis, however, higher skilled technique and diagnosis accuracy are requested.

If an apparatus which performs automatically and more objectively a rapid diagnosis that is conducted on cancer cells of extracted solid tissue, and that requires restraint for a predetermined period of time during an operation is developed, such an apparatus seems to be very useful for a pathologist. A rapid pathological diagnosis can be conducted only on one section. An analysis of tissue of tumor stump leads to a state where whole cells in the tissue can be analyzed. It is desired to develop and provide such an apparatus.

Therefore, there is a related-art cell analyzer in which fluorescence is detected from a measurement specimen flowing through a flow cell by using the flow cytometry method, and an abnormality of cells to be measured is determined based on a value in which the size of the to-be-measured cells is reflected, and that in which the size of the nuclei of the to-be-measured cells is reflected (see JP-A-2009-103687).

SUMMARY

It is therefore an object of the invention to provide a cell analyzer and a cell analyzation method which, by using a result of measurement by a flow cytometer, can analyze the malignancy grade of cancer very easily and highly accurately.

In order to achieve the object, according to the invention, there is provided a cell analyzer comprising: a measuring portion which measures cells that are nuclear stained; a displaying portion which displays a histogram of a fluorescence intensity by using a result of the measurement by the measuring portion; and a determining unit which obtains a number of strong-area cells that are distributed in an area where the fluorescence intensity is stronger than normal cells, and which determines a malignancy grade of cancer based on the number of strong-area cells and the histogram.

The determining unit may perform the determination based on a ratio of the number of strong-area cells to a number of cells obtained from the histogram.

A number of weak-area cells which are distributed in an area where the fluorescence intensity is weaker than the normal cells may be obtained from data of the histogram, and the determination by the determining unit may be corrected by the number of weak-area cells.

A number of weak-area cells which are distributed in an area where the fluorescence intensity is weaker than the normal cells may be obtained from data of the histogram, and the determination may be performed based on a ratio of the number of weak-area cells to the number of strong-area cells.

In order to achieve the object, according to the invention, there is also provided a cell analyzation method comprising: measuring cells that are nuclear stained, to obtain a histogram of a fluorescence intensity; detecting a peak of normal cells from data of the histogram; obtaining a number of strong-area cells that are distributed in an area where the fluorescence intensity is stronger than the peak of the normal cells; and determining a malignancy grade of cancer based on the obtained number of strong-area cells and the histogram.

The determination may be performed based on a ratio of the number of strong-area cells to a total number of cells.

A number of weak-area cells which are distributed in an area where the fluorescence intensity is weaker than the normal cells may be obtained, and the determination may be performed based on a ratio of the number of weak-area cells to the number of strong-area cells.

BRIEF DESCRIPTION OF THE DRAWINGS

FIG. 13 is a view showing comparison of results of a pathological analysis and analysis results by the embodiment of the cell analyzer of the invention.

DETAILED DESCRIPTION OF EMBODIMENTS

Figure 1:
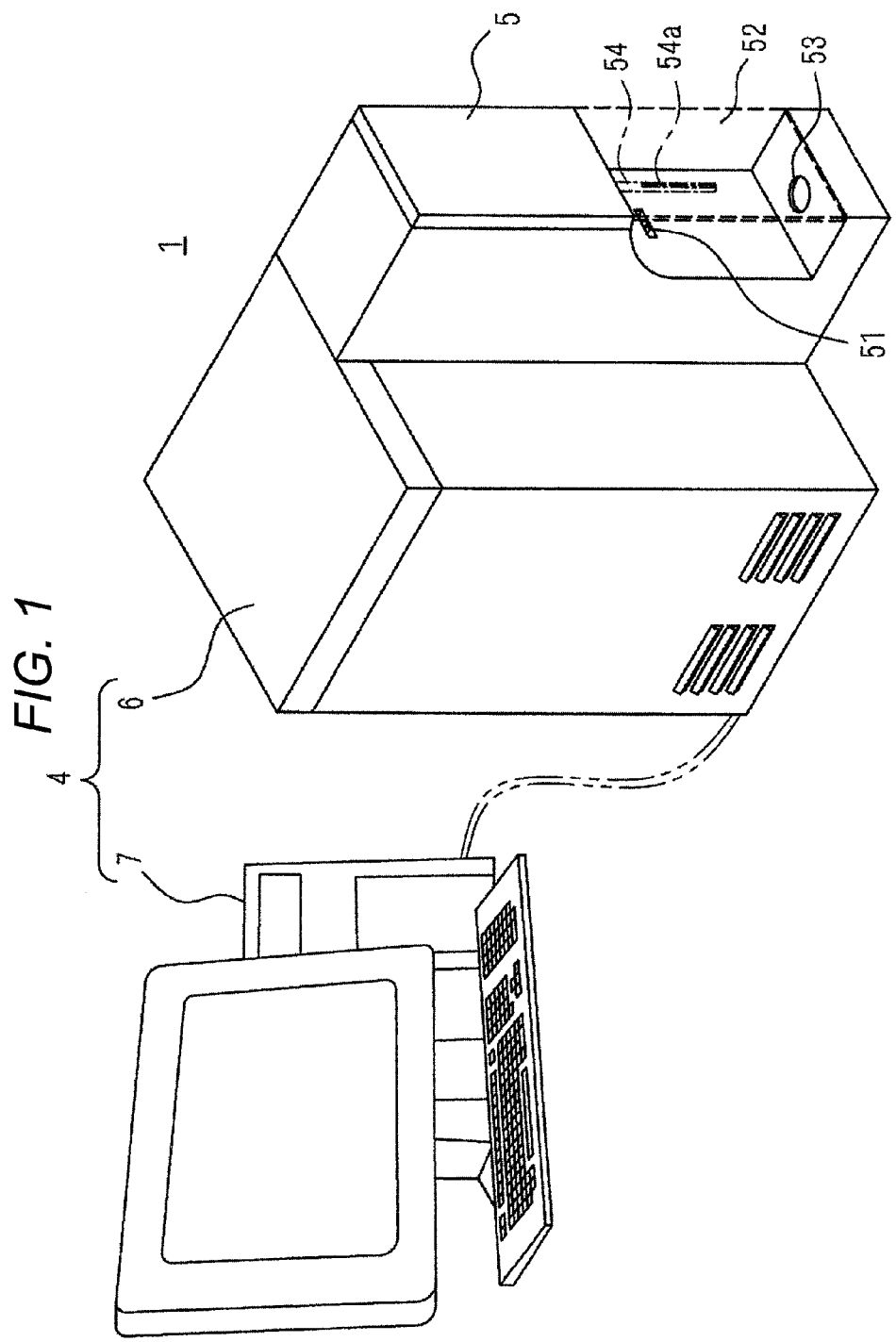
FIG. 1 is a schematic diagram of an analysis system which performs an analysis by using the method of the invention.
Figure 2:
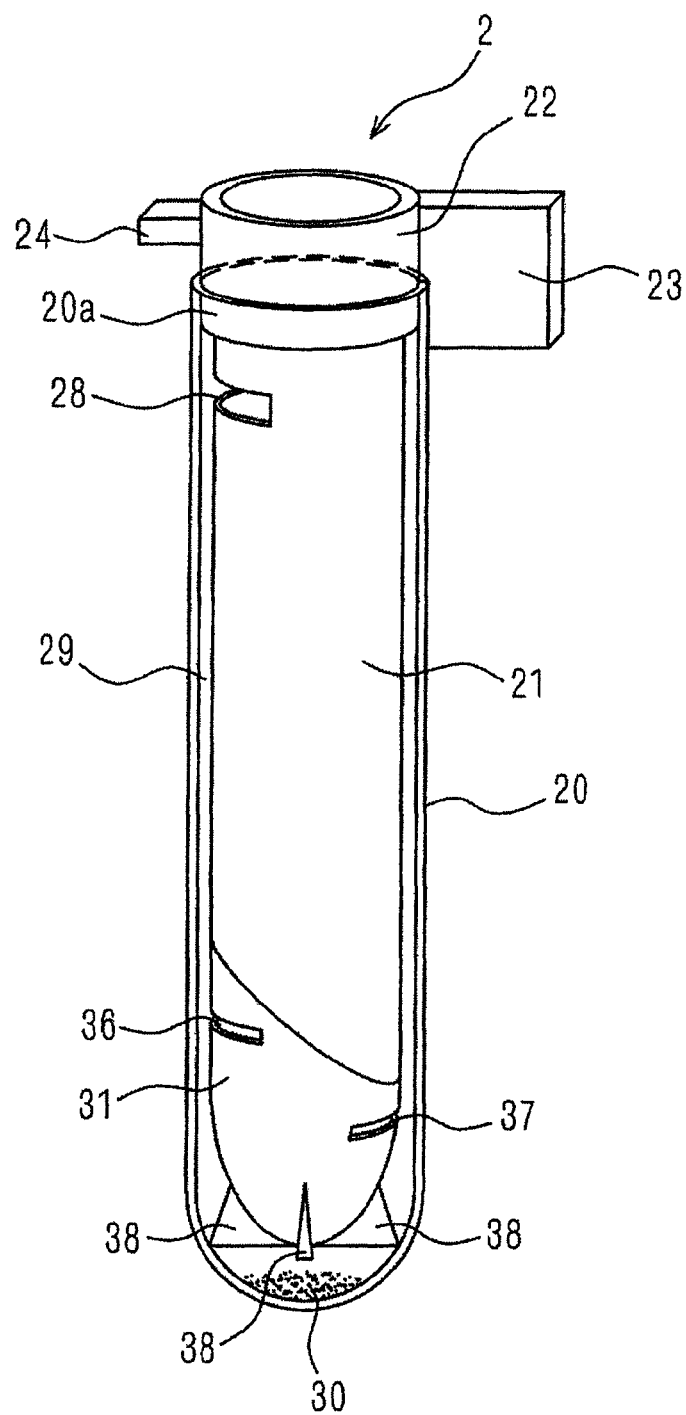
FIG. 2 is a side view showing a cell isolation apparatus which is used in all stages of analysis by the apparatus of the invention.

Hereinafter, an embodiment of a cancer cell analyzer and method of the invention will be described with reference to the accompanying drawings. In the figures, the identical components are denoted by the same reference numerals, and duplicated description will be omitted. FIG. 1 shows an analysis system 1 configured by a cell isolation apparatus 2, and a cancer malignancy grade analyzer 4 which is the cell analyzer of the invention. The malignancy grade analyzer 4 is configured by a flow cytometer 6 and a computer 7. It is a matter of course that, instead of the configuration where the flow cytometer and the computer are formed as separate apparatuses, the flow cytometer 6 may have the function of the computer 7. As shown in FIG. 2, the cell isolation apparatus 2 is set in an automatic cell pre-processing apparatus 5 in a state where it is inserted into a container 20 where a reagent is to be introduced.

Figure 3:
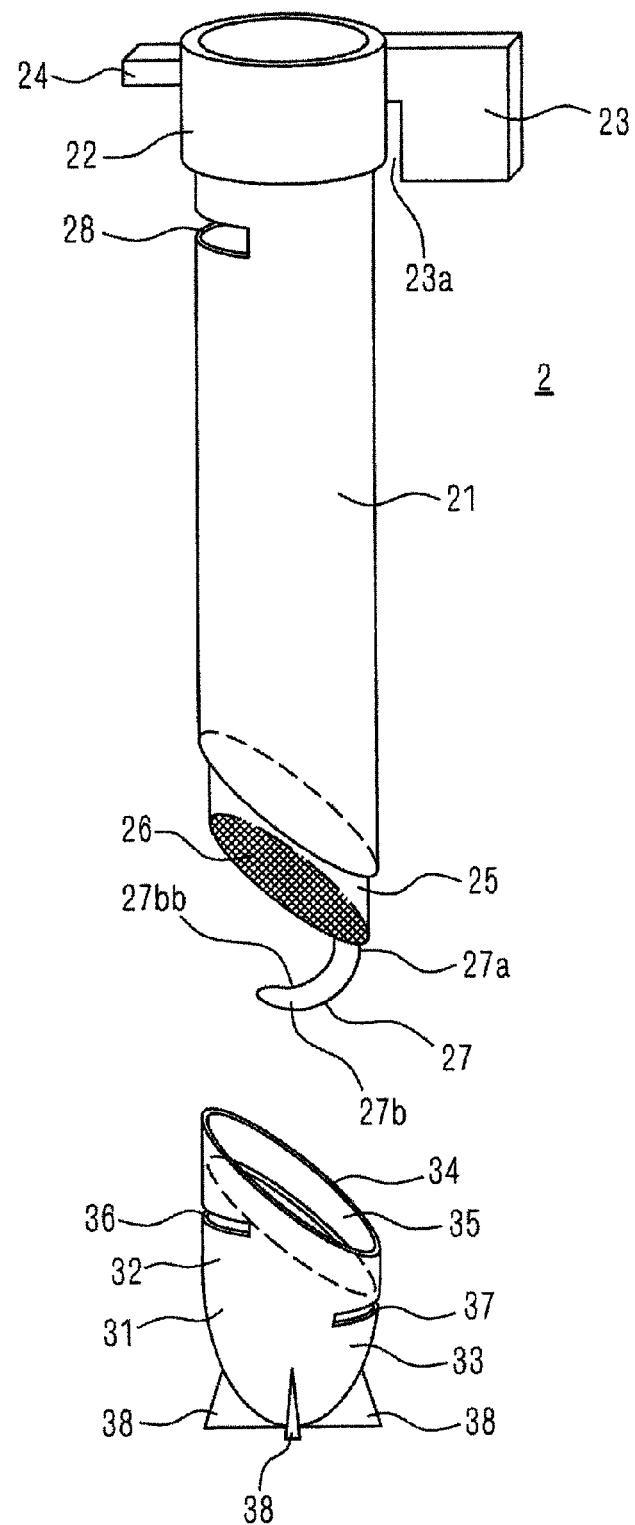
FIG. 3 is a sectional view of main portions of the cell isolation apparatus which is used in all stages of analysis by the apparatus of the invention.

As shown in FIG. 3, the cell isolation apparatus 2 includes a cylinder member 21 and bottom lid portion 31 which are made of a resin that is transparent or translucent, and that does not react with the agent. In the cylinder member 21, an upper portion has a thick band portion 22, and the outer diameter of the thick band portion 22 is substantially equal to the inner diameter of the container 20 into which the reagent is to be introduced, such as a test tube. The cylinder member is inserted into the container 20 in a state where the member is in contact with the inner wall of the mouth portion of the container.

Figure 4:
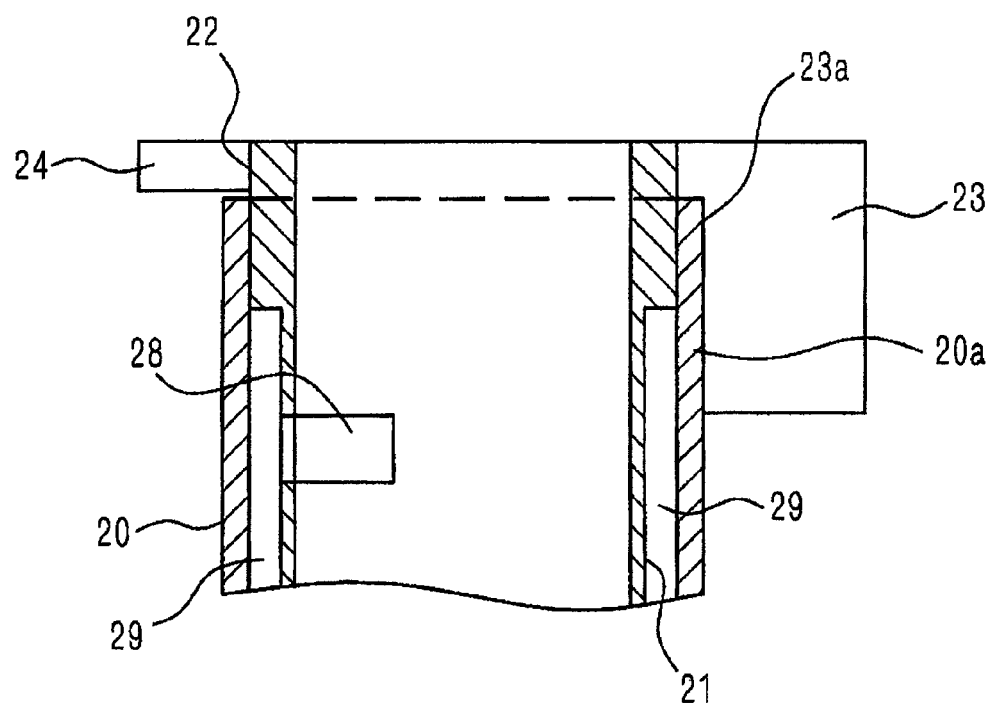
FIG. 4 is an assembly perspective view showing the cell isolation apparatus which is used in all stages of analysis by the apparatus of the invention.

As shown in FIGS. 3 and 4, on the outer wall of the thick band portion 22 of the cylinder member 21, nipping pieces 23, 24 are disposed at symmetric positions across the diameter of the cylinder member 21. A clamping groove 23a into which an end portion 20a of an opening portion of the container 20 enters and is clamped is formed between the nipping piece 23 and the thick band portion 22. The clamping groove 23a functions as a fitting portion for checking the attaching posture of the cell isolation apparatus 2 which is fitted to the container 20.

The nipping piece 24 has a shape which is different from that of the nipping piece 23. The cell isolation apparatus 2 in the state where the apparatus is inserted into the container 20 is set while, for example, the nipping piece 24 is inserted into a fixing hole 51 of the automatic cell pre-processing apparatus 5. A sensor such as a photo interrupter or a proximity switch is disposed in the fixing hole 51. The sensor sends a detection signal indicating whether the nipping piece 24 is adequately inserted or not, to a controlling portion, and, in the case that the piece is not adequately inserted, the controlling portion generates an alarm. Therefore, the nipping piece 24 and the nipping piece 23 can prevent the cell isolation apparatus 2 from being erroneously set in the automatic cell pre-processing apparatus 5.

A lower end portion of the cylinder member 21 is formed as a sleeve end portion 25 having a slightly-reduced diameter, and has a shape in which a part is cut away by an inclined surface. A net 26 is stretched over the inclined surface of the sleeve end portion 25 of the cylinder member 21. For example, the net 26 is made of a resin or a metal, has a roughness of a mesh diameter of 40 μm, and is stretched over the inclined surface of the sleeve end portion 25 by a welder or the like.

When the nipping piece 24 is set in the fixing hole 51 of the automatic cell pre-processing apparatus 5, the lowest portion of the net 26 is located in the front side, and, in the state which is shown in FIG. 1, and in which a nozzle 54 of the automatic cell pre-processing apparatus 5 is lowered, the tip end of the nozzle 54 is in close proximity to the lowest portion of the net 26. In the nozzle 54, a slit 54a is formed while extending from the tip end in the longitudinal direction (the vertical direction in FIG. 1). The nozzle is configured in a shape in which an incision is made in the tip end of the nozzle so that, during pipetting which will be described later, a trouble that the nozzle 54 is clogged with pulverized tissue and the pipetting is hindered is prevented from occurring.

A spoon 27 which is a tissue acquiring unit is projectingly formed on the lowest end portion of the sleeve end portion 25. The spoon 27 has a stem portion 27a which downward extends in a straight manner from the sleeve end portion 25, and a scraping portion 27b which is bent substantially perpendicularly from the tip end of the stem portion 27a toward the inner diameter side of the cylinder member 21. A center portion 27bb of the scraping portion 27b is formed into a recessed container-like shape which facilitates a work in the case where tissue is scraped and scraped tissue is held. The tissue acquiring unit is not limited to a spoon-like shape as far as these requirements are satisfied.

An air vent hole 28 is formed in the outer wall which is immediately below the thick band portion 22 of the cylinder member 21. In the case where a liquid is stored while starting from the bottom side, the air existing in a gap 29 between the cylinder member 21 and the container 20 escapes from the upper opening of the cylinder member 21 through the hole 28. Therefore, an adequate process of pipetting is ensured.

The bottom lid portion 31 is a bottomed pipe configured by a tubular body portion 32 and a hemisphere shell member 33. An open end portion 34 of the body portion 32 is formed as an inclined surface which is coincident with that of the sleeve end portion 25 of the cylinder member 21. An inner wall portion 35 of the open end portion 34 is formed as a thin inner wall into which the sleeve end portion 25 of the cylinder member 21 is inserted.

Holes 36, 37 through which the interior communicates with the exterior are formed in upper and lower sides of the body portion 32. Also in the state where the sleeve end portion 25 is inserted into the bottom lid portion 31, the holes 36, 37 cause the interior and the exterior to communicate with each other to allow the liquid which flows into the body portion 32 to flow out into the gap 29 between the cylinder member 21 and the container 20. In the case where a cell suspension is sucked by pipetting, the holes function so as to bring the liquid back from the gap 29 between the cylinder member 21 and the container 20.

Moreover, there may be a case where stirring of tissue is hindered by bubbles which are produced by pipetting. In this case, the existence of the holes 36, 37 can extract bubbles from the hole 36 and introduce the liquid through the hole 37. Furthermore, since the net 26 is inclined, air evacuation through the net 26 can be efficiently performed.

Leg portions 38 which butt against the wall of the container 20 to stabilize the posture are disposed on the outer wall of the hemisphere shell member 33. The leg portions 38 have a substantially triangular shape, and butt against the bottom and inner side walls of the container 20 to cooperate with the thick band portion 22, thereby holding the cell isolation apparatus 2 in a stabilized state without causing the cell isolation apparatus to fluctuate in the container 20. The leg portions are not limited to have the triangular shape, and may have any shape as far as the cell isolation apparatus 2 can be held in a stabilized state.

In the case where a cell suspension is to be obtained by using the thus configured cell isolation apparatus 2, the container 20 in which a cell treating chemical 30 is introduced is used. As the cell treating chemical 30, for example, a reagent can be used which is produced by mixing 10% Triton X-100/R0 water, 1% propidium iodine/R0 water, and 1% RNase/R0 water at a rate of 1:10:2 (volume) to obtain a solution, dispensing 65 μL of the solution into a test tube, and then freeze drying the dispensed solution by using a freeze drying machine (KYOWA VAC RLE-52ES: manufactured by KYOWA VACUUM ENGINEERING, CO., LTD). The detail of the reagent is described in Japanese Patent Application No. 2009-244702 (JP-A-2010-204086) which was filed by the inventors of the present application. It is a matter of course that the reagent is not limited to a freeze dried one. In the case of a liquid reagent, the reagent may be supplied from the automatic cell pre-processing apparatus 5. Furthermore, dextrin may be added to the reagent.

Figure 5:
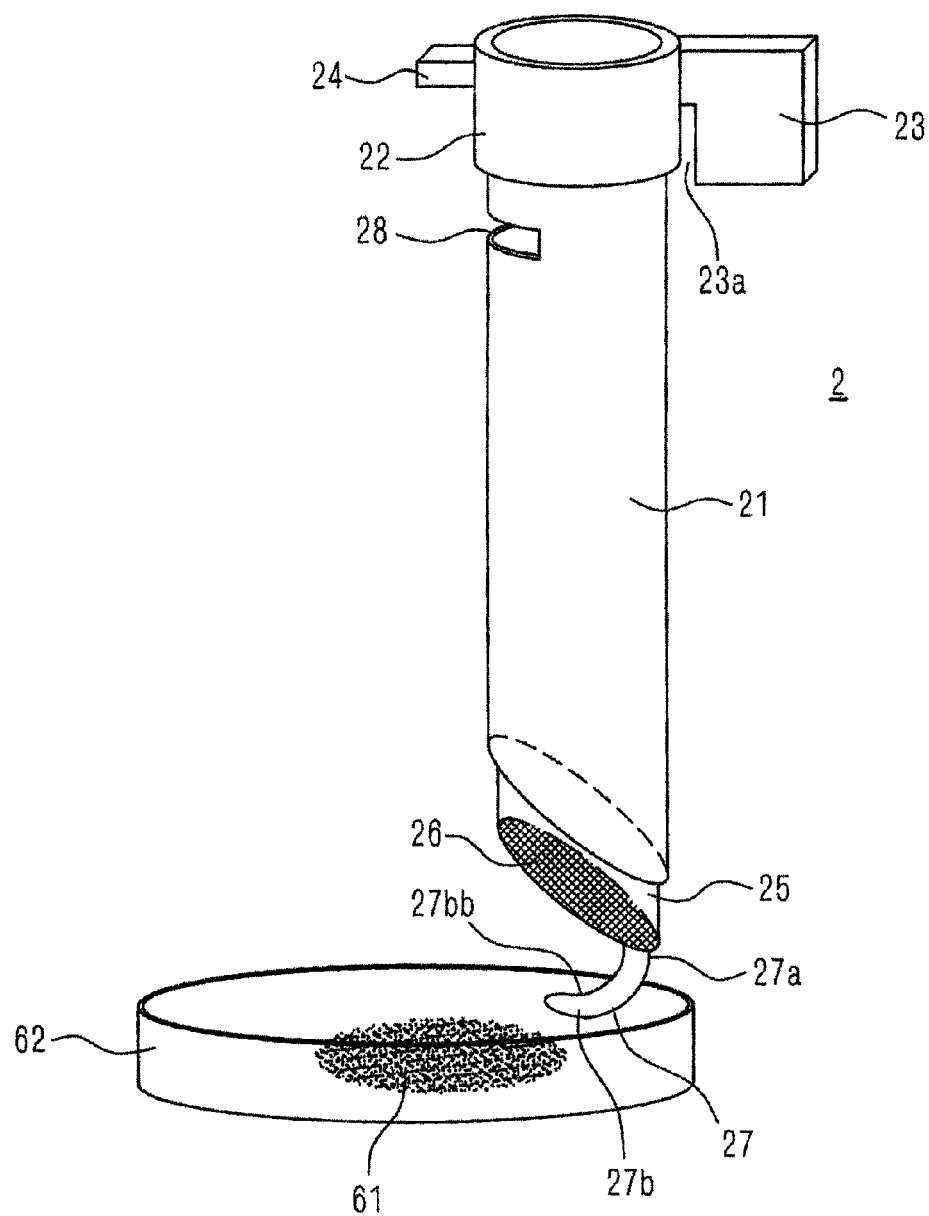
FIG. 5 is a perspective view showing a process of introducing tissue in the cell isolation apparatus which is used in all stages of analysis by the apparatus of the invention.

As shown in FIG. 5, tissue 61 which is to be analyzed is placed in a petri dish 62, and an adequate amount of the tissue is scraped by the spoon 27 of the cylinder member 21. Then, the bottom lid portion 31 is coupled to the cylinder member 21 in the state where the tissue is placed on the spoon 27. Thereafter, the cell isolation apparatus 2 is inserted and fitted into the container 20 which contains the cell treating chemical 30. In this way, by the cell isolation apparatus 2, tissue can be easily scooped without using another tool such as a tweezers, and set in a measuring kit.

In the automatic cell pre-processing apparatus 5 shown in FIG. 1, next, a lid 52 which can be vertically slid is opened, the nipping piece 24 of the cell isolation apparatus 2 is inserted into the fixing hole 51, and a bottom portion of the container 20 is inserted into a positioning hole 53, thereby setting the cell isolation apparatus so that the container 20 is adequately supported.

Figure 6:
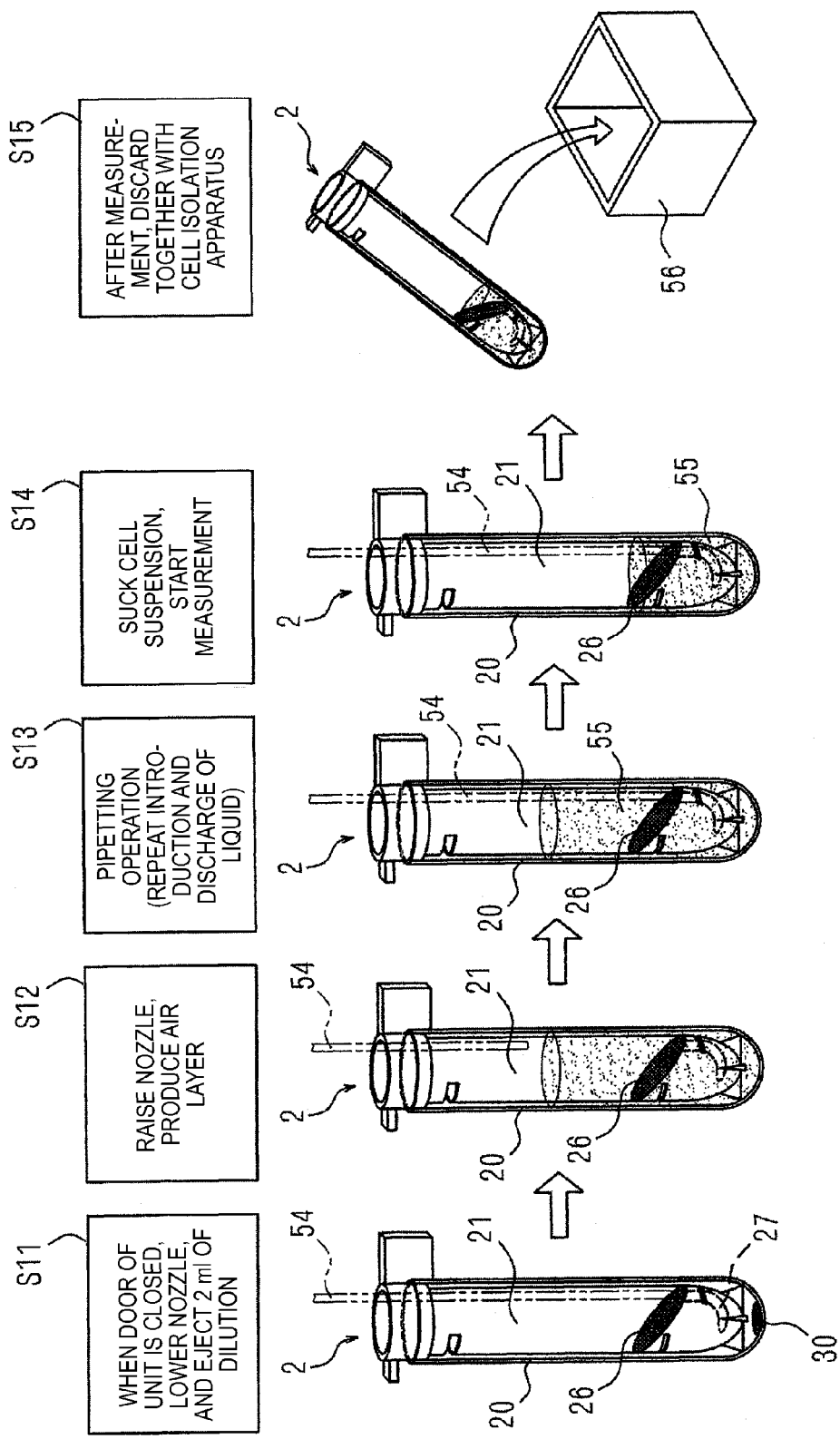
FIG. 6 is a step view showing a process of producing a cell suspension by using the cell isolation apparatus which is used in all stages of analysis by the apparatus of the invention.

When the lid 52 of the automatic cell pre-processing apparatus 5 is thereafter closed, the automatic cell pre-processing apparatus 5 performs a pre-processing operation as shown in FIG. 6. First, the automatic cell pre-processing apparatus 5 lowers the nozzle 54 and ejects 2 ml of a phosphate buffer solution which is a diluted solution (S11). Next, the nozzle 54 is raised, and an air layer is produced from the nozzle 54 in a suction/ejection mechanism portion of the automatic cell pre-processing apparatus 5 (S12).

The nozzle 54 is again lowered, and pipetting for introducing and discharging a cell suspension 55 in which the reagent 30, the phosphate buffer solution, and the tissue 61 are mixed together is performed for a predetermined time period (S13). When the predetermined time period was set to be about 5 minutes in measurement of brain tumor tissue, a sufficient result was obtained. Next, the cell suspension 55 which is used as a specimen is sucked in the state where the nozzle 54 is lowered, and measurement by the flow cytometer 6 is started (S14). The sucked cell suspension is obtained as one which is filtered by the net 26.

When the measurement is ended, the automatic cell pre-processing apparatus 5 informs of the end by, for example, a warning sound, and the operator opens the lid 52 of the automatic cell pre-processing apparatus 5, takes out the container 20 in the state where the cell isolation apparatus 2 is set, and then discards all of them into a dust box 56 for medical waste (S15).

The cell suspension sucked by the automatic cell pre-processing apparatus 5 is sent to the flow cytometer 6 constituting the malignancy grade analyzer 4. By using the cell suspension, the flow cytometer 6 measures cells which are isolated and nuclear stained, and obtains a scattergram which is not shown, from the peak value of a fluorescent signal at each event, and an integrated value. An adequate gating process is performed on the scattergram to obtain a histogram of integrated values of the fluorescence intensity from events which seem to be a single cell. The histogram is displayed on a display device which is not shown, such as an LCD. As described above, the flow cytometer 6 functions as a measuring portion which measures cells that are nuclear stained, and a displaying portion which displays a histogram of the fluorescence intensity by using a result of the measuring portion.

Figure 7:
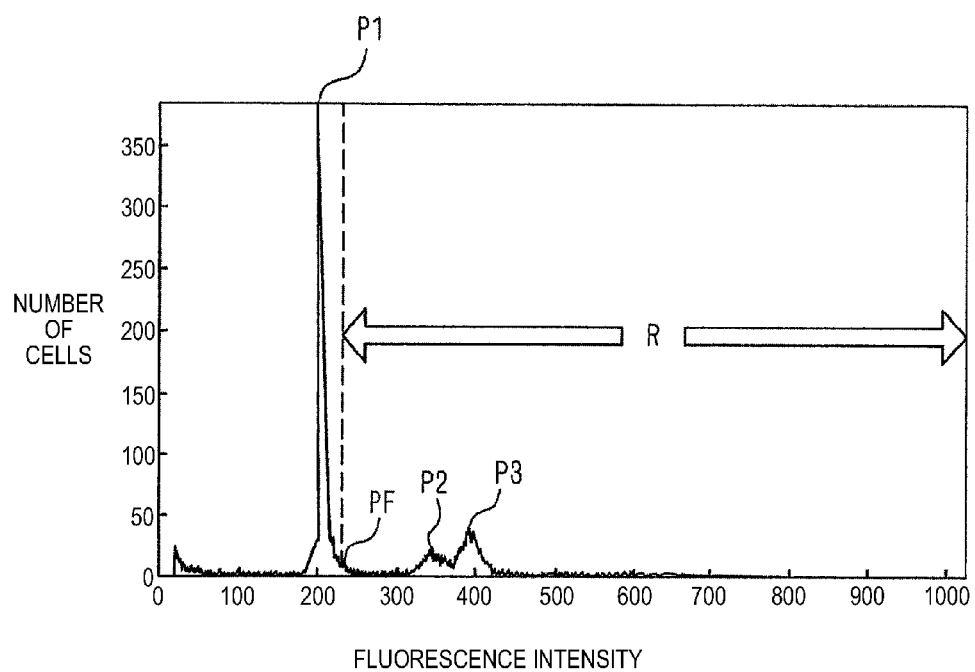
FIG. 7 is a view showing an example of a histogram of the fluorescence intensity produced by a flow cytometer.

The histogram is as shown in FIG. 7. In the figure, P1 indicates a peak due to groups of G0/G1 phase cells, P2 indicates a peak due to cell groups of DNA Aneuploidy indicating tumor cells which are different in amount of DNA from normal cells, and P3 indicates a peak due to groups of G2/M phase cells. Data of the histogram of the fluorescence intensity obtained by the flow cytometer 6 are sent to the computer 7.

The computer 7 includes a determining unit. The determining unit obtains the number of strong-area cells which are distributed in an area where the fluorescence intensity is stronger than normal cells, and determines the cancer malignancy grade based on the number of strong-area cells and the histogram.

Figures 8, 9:
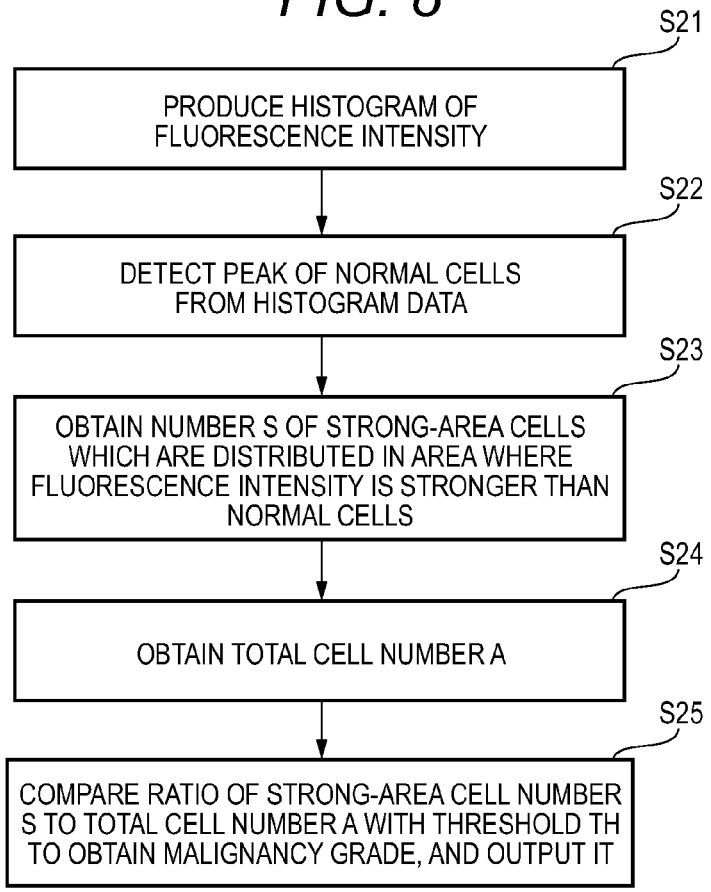
FIG. 8 is a flowchart illustrating the operation of an embodiment of the cell analyzer of the invention.
FIG. 9 is a view showing thresholds which are used in the embodiment of the cell analyzer of the invention.

The operation of the malignancy grade analyzer 4 configured by the flow cytometer 6 and the determining unit of the computer 7 can be indicated by the flowchart shown in FIG. 8. A step of producing the histogram of the fluorescence intensity (S21) is performed by the flow cytometer 6.

Next, the determining unit detects a peak of normal cells from the histogram data (S22). Namely, the peak P1 due to groups of G0/G1 phase cells shown in FIG. 7 is obtained, and the end point PF of the peak is determined. Specifically, a point where the number of cells is equal to or smaller than a predetermined number (for example, 10) is searched.

Next, the number S of strong-area cells which are distributed in an area where the fluorescence intensity is stronger than normal cells is obtained (S23). In FIG. 7, the number of cells which are distributed in an area R indicated in the right side of PF is obtained. Furthermore, the total cell number A in the histogram of the fluorescence intensity is obtained (S24). In this case, a ratio (S/A) of the strong-area cell number S to the total cell number A is compared with a threshold TH to obtain the malignancy grade, and the malignancy grade is output on the display device of the computer 7 or by a printer which is not shown (S25).

FIG. 9 shows the threshold TH. The threshold was obtained in the following manner. A pathological analysis was actually performed, results were classified into the normal and grades 2 to 4, and the ratio (S/A) of the strong-area cell number S was plotted to obtain the distribution shown in FIG. 10. In the result, for each of the normal and grades 2 to 4, the mean and the standard deviation were obtained as shown in FIG. 11. Calculations were conducted by using the obtained respective means and standard deviations, and the threshold TH of FIG. 9 was obtained.

Figure 10:
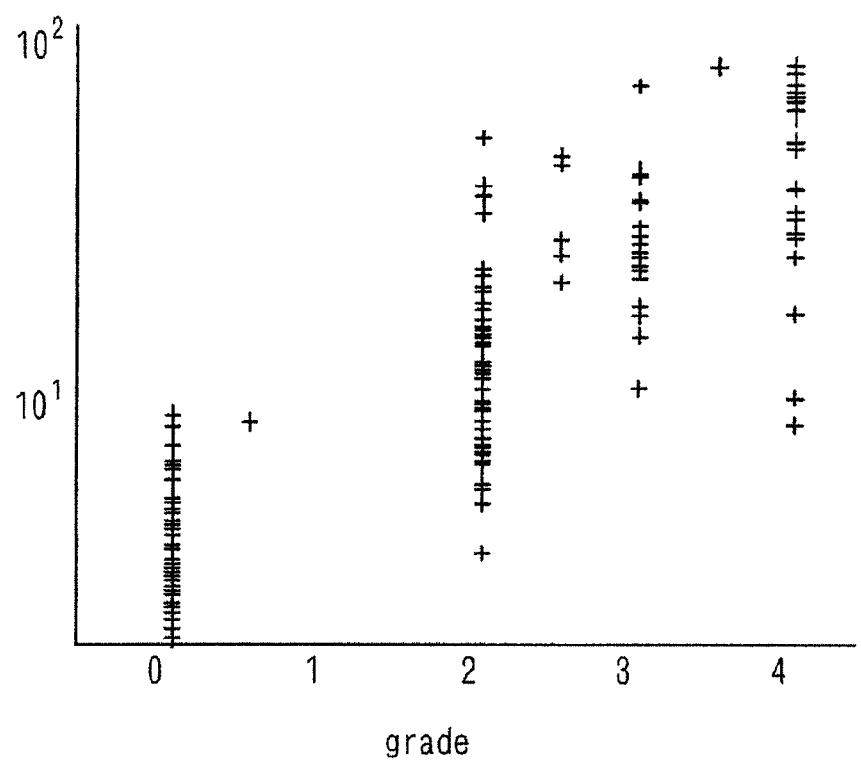
FIG. 10 is a view in which results of the cancer malignancy grade analysis according to a pathological analysis are plotted.
Figure 11:
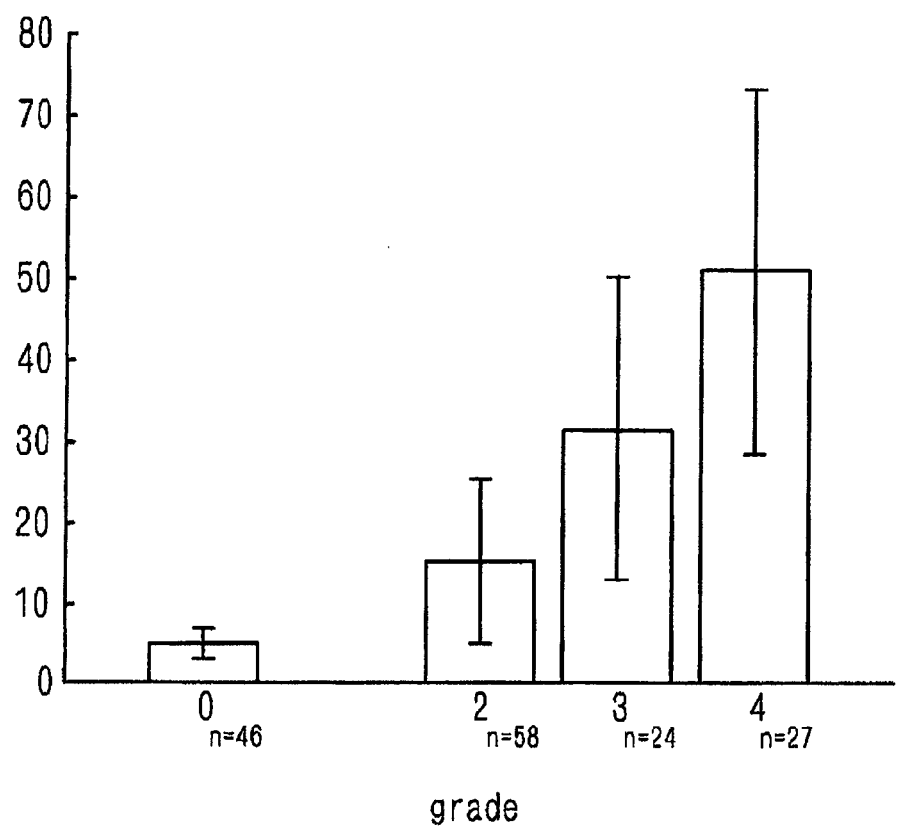
FIG. 11 is a view showing the mean and the standard deviation obtained from FIG. 9.
Figure 12:
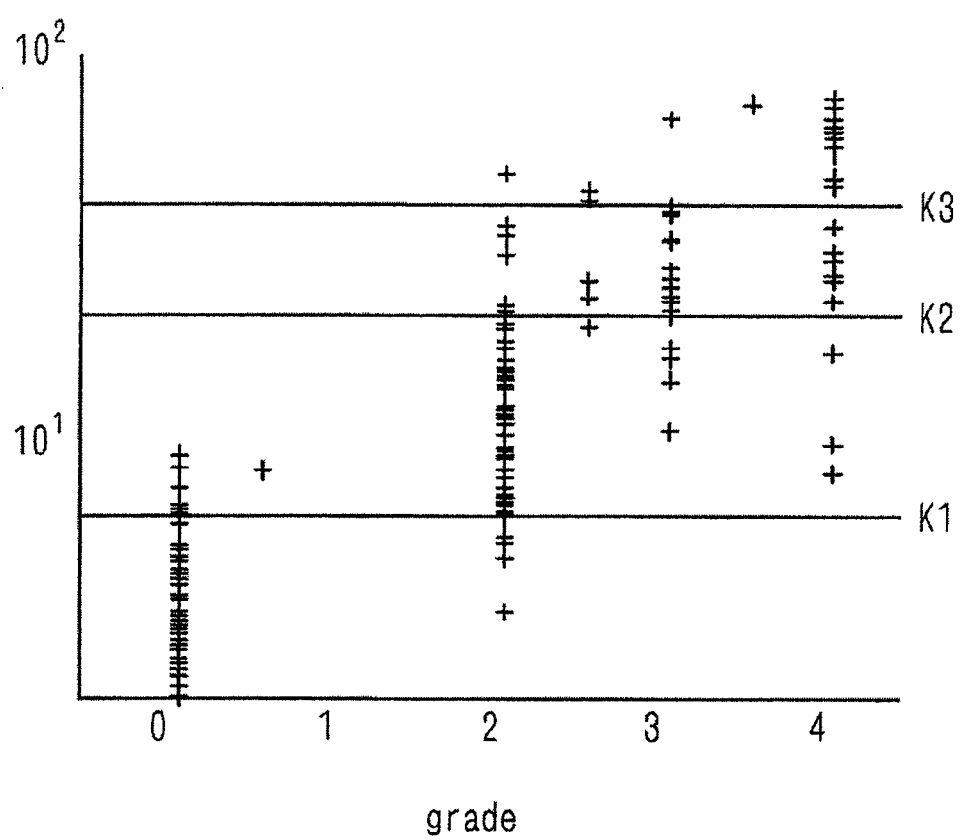
FIG. 12 is a view showing FIG. 10 together with boundary lines of thresholds.

With respect to the distribution of results of the pathological analysis shown in FIG. 10, boundary values K1 (6.1%), K2 (20.6%), and K3 (40%) of the threshold TH are illustrated as shown in FIG. 12. FIG. 13A shows a table in which, with respect to the normal (0) and grades 2 to 4 obtained as results of the pathological analysis, results which were obtained by performing the cell analyzation method of the embodiment are shown while being decomposed in the lateral direction of the figure. With respect to 46 cases in which the result of the pathological analysis was the normal (0), results of the analysis according to the embodiment show 36 cases of the normal (0) and 10 cases of grade 2. According to the embodiment, it was confirmed that, as shown in "True negative" in FIG. 13B, normality is determined with a probability of 78%, and, as shown in "False positive" in FIG. 13B, it is determined that the malignancy grade exists, with a probability of 22%.

With respect to 109 cases in which the result of the pathological analysis was either of grades 2 to 4, in the embodiment, it was confirmed that, as shown in "False negative" in FIG. 13B, normality is determined with a probability of 5%, and, as shown in "True positive" in FIG. 13B, it is determined that the malignancy grade is either of grades 2 to 4.

The threshold TH which is used in the embodiment described above can be adequately changed in accordance with the tissue to be analyzed. In the above, the determination is performed by using the ratio (S/A) of the strong-area cell number S to the total cell number A. Alternatively, the number W of weak-area cells which are distributed in an area where the fluorescence intensity is weaker than normal cells is obtained, and the determination may be performed with weighting based on a ratio of the weak-area cell number W to the strong-area cell number S. In other words, it is meant that the determination by the determining unit is corrected by using the weak-area cell number. Moreover, various techniques such that the total cell number A, the strong-area cell number S, and the weak-area cell number W are combined with one another to obtain a difference, and the malignancy grade is determined by using the difference may be employed.

In the above, the determination of the cancer malignancy grade in which either of the normal and the grades is determined has been described. It is a matter of course that the invention can be used in determination in which it is simply determined whether cancer cells exist or not.

According to an aspect of the invention, the number of strong-area cells which are distributed in an area where the fluorescence intensity is stronger than normal cells is obtained from the histogram of the fluorescence intensity, and the malignancy grade of cancer is determined based on the number of strong-area cells and the histogram. Therefore, the malignancy grade of cancer can be easily analyzed by using a result obtained by a flow cytometer.

What is claimed is:

1. A cell analyzer comprising:
   a cytometric device which measures cells that are nuclear stained;
   a display which displays a histogram of a fluorescence intensity by using a result of the measurement by the cytometric device; and
   a computer comprising at least one processor configured to obtain a number of strong-area cells that are distributed in an area where the fluorescence intensity is stronger than normal cells, and determine a malignancy grade of cancer using the number of strong-area cells and the histogram.

2. The cell analyzer according to claim 1, wherein the computer comprising the at least one processor performs the determination using a ratio of the number of strong-area cells to a number of cells obtained from the histogram.

3. The cell analyzer according to claim 2, wherein a number of weak-area cells which are distributed in an area where the fluorescence intensity is weaker than the normal cells is obtained from data of the histogram, and the determination by the computer comprising the at least one processor is corrected by the number of weak-area cells.

4. The cell analyzer according to claim 1, wherein a number of weak-area cells which are distributed in an area where the fluorescence intensity is weaker than the normal cells is obtained from data of the histogram, and the determination is performed using a ratio of the number of weak-area cells to the number of strong-area cells.

5. A cell analyzation method comprising:
   measuring, by a cytometric device, cells that are nuclear stained, to obtain a histogram of a fluorescence intensity;
   detecting a peak of normal cells from data of the histogram;
   obtaining, by a computer comprising at least one processor, a number of strong-area cells that are distributed in an area where the fluorescence intensity is stronger than the peak of the normal cells; and
   determining a malignancy grade of cancer using the obtained number of strong-area cells and the histogram.

6. The cell analyzation method according to claim 5, wherein the determination is performed using a ratio of the number of strong-area cells to a total number of cells.

7. The cell analyzation method according to claim 5, wherein a number of weak-area cells which are distributed in an area where the fluorescence intensity is weaker than the normal cells is obtained, and the determination is performed using a ratio of the number of weak-area cells to the number of strong-area cells.

8. A cell analyzer comprising:
   at least one processor configured to control measurement of cells that are nuclear stained, generation of a histogram of a fluorescence intensity by using a result of the measurement, determination of a number of strong-area cells that are distributed in an area where the fluorescence intensity is stronger than normal cells, and determination of a malignancy grade of cancer using the number of strong-area cells and the histogram.

* * * * *